(12) United States Patent
Kanazawa et al.

(10) Patent No.: US 7,745,690 B2
(45) Date of Patent: Jun. 29, 2010

(54) TRANSGENIC NONHUMAN MAMMAL REPRESENTING THE PATHOLOGIC CONDITIONS OF HUMAN RHEUMATOID ARTHRITIS

(75) Inventors: Satoshi Kanazawa, Nagoya (JP); Takashi Okamoto, Nagoya (JP)

(73) Assignee: Nagoya Industrial Science Research Institute, Nagoya-shi (JP)

( * ) Notice: Subject to any disclaimer, the term of this patent is extended or adjusted under 35 U.S.C. 154(b) by 260 days.

(21) Appl. No.: 10/591,993

(22) PCT Filed: Mar. 8, 2005

(86) PCT No.: PCT/JP2005/004007

§ 371 (c)(1),
(2), (4) Date: Sep. 7, 2006

(87) PCT Pub. No.: WO2005/085438

PCT Pub. Date: Sep. 15, 2005

(65) Prior Publication Data
US 2007/0199083 A1    Aug. 23, 2007

(30) Foreign Application Priority Data
Mar. 9, 2004  (JP) .............................. 2004-066218

(51) Int. Cl.
*A01K 67/027* (2006.01)
*A01K 67/00* (2006.01)
*A01K 67/033* (2006.01)

(52) U.S. Cl. .................. 800/18; 800/8; 800/9; 800/13; 800/14

(58) Field of Classification Search ....................... None
See application file for complete search history.

(56) References Cited

FOREIGN PATENT DOCUMENTS

WO    WO98/15626    *    4/1998

OTHER PUBLICATIONS

Kappel et al (1992) Current Opinion in Biotechnology 3, 548-553.*
Mullins et al (1993) Hypertension 22, p. 630-633.*
Houdebine (1994) J. Biotech. 34, p. 269-287.*
Mullins et al. (J. Clin. Invest.1996; 98, p. 1557-1560.*
Cameron (1997) Molec. Biol. 7, p. 253-265.*
Sigmund (2000) Arteroscler. Throm. Vasc. Biol. 20, p. 1425-1429.*
Niemann (1998) Transg. Res. 7, p. 73-75.*
Moreadith et al., J. Mol. Med., 1997, p. 208-216.*
Pera et al. [Journal of Cell Science 113: 5-10 (2000)].*
Wall (1996) Theriogenology 45, 57-68.*
Osaki et al. (Biochemical Journal. Sep. 11, 2002; 1-34).*
Lindqvist et al. (Trends in Genetics. 2002; S7-S13).*
Otten et al. (Journal of Immunology. 2003; 170: 1150-1157).*
Harton et al. (Molecular and Cellular Biology, Sep. 2000; 20(17):6185-6194).*
(Kanazawa et al. PNAS, Sep. 26, 2006; 103(39): 14465-14470).*
Reith et al. (Annual Review Immunology. 2001; 19: 331-3373).*
Kanazawa et al. (International Immunology. 2001; 13(7): 951-958).*
LeibundGut-Landmann et al. (Eur. J. Immunol. 2004; 34:1513-1525).*
Ting et al. (Cell Aptil 2002;S21-S33).*
M. Feldmann; "Pathogenesis of arthritis: recent research progress;" *Nature Immunology*; vol. 2; No. 9; Sep. 2001; pp. 771-773/Discussed in the specification.
P. H. Wooley, et al; "Type II Collagen-Induced Arthritis in Mice;" *J. Exp. Med.*; vol. 154; Sep. 1981; pp. 688-700./Discussed in the specification.
H. Kim, et al; "Thyrotropin-Mediated Repression of Class II *Trans*-Activator Expression in Thyroid Cells: Involvement of STAT3 and Suppressor of Cytokine Signaling;" *The Journal of Immunology*; vol. 171; No. 2; 2003; pp. 616-627.
A. N. Santos, et al.; "Constitutive expression of HLA class II mRNA in synovial fibroblast-like cells from patients with rheumatoid arthritis;" *Immunology Letters*; vol. 58; No. 1; 1997; pp. 53-58.
A. N. Santos, et al.; "Regulation by transforming growth factor-β1 of class II mRNA and protein expression in fibroblast-like synoviocytes from patients with rheumatoid arthritis;" *International Immunology*; vol. 10; No. 5;1998; pp. 601-607.
V. Lefebvre, et al.; "An 18-Base-Pair Sequence in the Mouse Proα1(II) Collagen Gene Is Sufficient for Expression in Cartilage and Binds Nuclear Proteins That Are Selectively Expressed in Chondrocytes;" *Molecular and Cellular Biology*; vol. 16; No. 8; Aug. 1996; pp. 4512-4523.
G. Zhou, et al.; Three High Mobility Group-like Sequences within a 48-Base Pair Enhancer of the *Col2a1* Gene Are Required for Cartilage-specific Expression in Vivo; *The Journal of Biological Chemistry*; vol. 273; No. 24; June 12, 1998; pp. 14989-14997.

(Continued)

*Primary Examiner*—Scott Long
(74) *Attorney, Agent, or Firm*—Edwards Angell Palmer & Dodge LLP

(57) ABSTRACT

It is intended to provide a transgenic nonhuman mammal well representing the pathologic conditions of human rheumatoid arthritis. A transgenic nonhuman mammal is obtained by transferring a foreign DNA, wherein a DNA selected from the group consisting of an MHC class II transcriptional activator gene, the activity domain of an MHC class II transcriptional activator gene and a variant of an MHC class II transcriptional activator gene is provided under the control of a type II collagen promoter, into a cell at the early stage of development.

1 Claim, 7 Drawing Sheets

OTHER PUBLICATIONS

G. Zhou, et al.; "A 182 bp fragment of the mouse proα1(II) collagen gene is sufficient to direct chonodrocyte expression in transgenic mice;" *Journal of Cell Science*; vol. 108; No. 12; 1995; pp. 3677-3684.

K. Kakimoto, et al.; Tokushu II Mansei Kansetsu Rheumatism (RA) ni Okeru Saikin no Topics Collagen Yudo Kansetsuen to T-saibo Kogen Juyotai; *Clinical Immunology*; vol. 26; No. 2; 1994; pp. 171-177 and end sheet (8 Sheets total).

* cited by examiner

FIG. 3

0: No symptoms were observed

1: Redness + slight joint swelling (two joints or less)

2: Redness + moderate joint swelling (three joints or more)

3: Redness + severe joint swelling + dyskinesia

Evaluate each extremity by scoring from 0 to 3 and calculate total score of four extremities (max=12)

When total score is 4 or more, it is determined that rheumatoid arthritis is developed.

(B)

(A)

TRANSGENIC NONHUMAN MAMMAL REPRESENTING THE PATHOLOGIC CONDITIONS OF HUMAN RHEUMATOID ARTHRITIS

TECHNICAL FIELD

The present invention relates to a transgenic non-human mammal. More specifically, the present invention relates to a transgenic non-human mammal representing pathologic conditions of human rheumatoid arthritis.

BACKGROUND ART

Conventionally, in the development of drugs (antirheumatic drugs) for human rheumatoid arthritis (human articular rheumatism), type II collagen arthritis model mice and the like have been used. In H-$2^q$ or H-$2^r$ haplotype mice, by administering 0.1 to 0.2 mg of type II collagen by subcutaneous injection, symptoms of rheumatoid arthritis are induced (collagen-induced arthritis, CIA). In frequently used H-$2^q$ haplotype mice, arthritis is usually observed by conducting secondary immunization after primary immunization. In several days after the secondary immunization, rheumatoid symptoms are presented including that acute phase inflammation occurs in a local region of the joint and then a series of chronic inflammation is elicited. Human rheumatoid arthritis is a disease whose main symptoms include inflammation in the joints, bone destruction, ankylosis and deformity of bones, and the like. In general, the disease tends to show a high chronicity. Furthermore, since human rheumatoid arthritis is often complicated with angiitis, it may induce myocarditis, interstitial pneumonia, peripheral angiitis, and the like. These complications are refractory. Therefore, development of specific treatment methods has been demanded.

SUMMARY OF THE INVENTION

Problems to be Solved by the Invention

In CIA using H-$2^q$ haplotype mice, arthritis is completed for a short time. Therefore, it is difficult to sequentially follow the chronic, lingering and progressive symptoms, which are found in human rheumatoid arthritis, and in particular, the change of pathologic conditions from the early stage to middle and late stages of rheumatoid arthritis in which inflammation gradually proceeds. In this way, a model mouse using H-$2^q$ haplotype mouse and the like is not satisfactory as a model animal of human rheumatoid arthritis. Under such circumstances, creation of a model animal representing the pathologic conditions of human rheumatoid arthritis more satisfactorily (i.e., an animal presenting more similar pathologic conditions of human rheumatoid arthritis) have been long awaited.

[Non-patent document 1] Feldmann M. 2001. Pathogenesis of arthritis: recent research progress. *Nat Immunol.* 9:771.

[Non-patent document 2] Wooley, P. H., H. S. Luthra, J. M. Stuart, and C. S. David. 1981. Type II collagen induced arthritis in mice. I. Major histocompatibility complex (I-region) linkage and antibody correlates. *J. Exp. Med.* 154:688.

Means to Solve the Problems

In view of the above-mentioned problems, the present inventors have attempted to produce a model animal of human rheumatoid arthritis by genetic engineering techniques. The onset of human rheumatoid arthritis is significantly correlated with specific major histocompatibility complex class II (referred to as "MHC class II" in this specification). Therefore, it is thought that an immunization reaction based on antigen presentation via the ectopic expression of MHC class II is profoundly involved in the onset mechanism of rheumatism. The present inventors have focused on this point and produced a transgenic mouse expressing an MHC class II transactivator gene (also referred to as "CIITA gene" in this specification) by using a promoter region of type II collagen showing articular cartilage-specific expression. The present inventors have succeeded in creating a model mouse developing arthritis frequently, by conducting backcross of this CIITA transgenic mouse onto an H-$2^q$ haplotype mouse that is highly responsive to type II collagen inducing rheumatoid arthritis. In this CIITA transgenic mouse, even when type II collagen with low concentration that is 1/20 with respect to the concentration of the type II collagen generally used in a CII inducing arthritis model (collagen-induced arthritis, CIA) is administered by subcutaneous injection, rheumatoid inflammation can be sufficiently observed. That is to say, it is determined that the transgenic mouse has a high sensitivity with respect to antigen such as type II collagen by a joint-specific ectopic expression of the MHC class II gene group. At this concentration, control mice (mice having the same genetic background or being litters but having no transgene) do not show the symptoms of rheumatoid arthritis. On the other hand, the symptoms of arthritis have gradually progressed over such a long time as several weeks to several months. Therefore, use of this transgenic mouse enables an accurate observation of the process of inflammation associated with rheumatoid arthritis. This means that the transgenic mouse is significantly effective as a model of human rheumatoid arthritis.

From the results mentioned above, findings that by carrying out gene modification so that the CIITA gene is expressed by the effect of a type II collagen promoter, a model animal that well represents pathologic conditions of human rheumatoid arthritis can be produced is obtained. The present invention has been made based on the above-mentioned findings and provides the following configuration.

[1] A transgenic non-human mammal including a foreign DNA, the foreign DNA having a DNA which is selected from the group consisting of an MHC class II transactivator gene, an active region of the MHC class II transactivator gene, and a mutant of the MHC class II transactivator gene (having a master switch function for controlling an expression of the MHC class II genes) and which is located under the control of a type II collagen promoter.

[2] The transgenic non-human mammal described in [1], wherein the foreign DNA includes a type II collagen enhancer.

[3] The transgenic non-human mammal described in [1] or [2], wherein a pathologic condition of human rheumatoid arthritis are presented by administration of type II collagen.

[4] The transgenic non-human mammal described in any of [1] to [3], wherein the pathologic condition of human rheumatoid arthritis are presented by twice or more administration of type II collagen in which a dose of the type II collagen for each administration is set to 0.01 mg to 0.05 mg.

[5] The transgenic non-human mammal described in any of [1] to [4], wherein the pathologic condition of human rheumatoid arthritis is a pathologic condition showing one or more of the following (1) to (7):

(1) Joint swelling is observed in three places or more in the whole body;
(2) Symmetry joint swelling is observed;
(3) Joint swelling lasting for a week or more is observed;
(4) Destruction, anktlosis, or deformity of bones in the extremities is observed;
(5) Infiltration of lymphoid cells is observed;
(6) Cartilage destruction and bone destruction due to formation of granulation tissue are observed; and
(7) Joint deformity progresses through early stage (stage I) and moderate stage (stage II).

[6] The transgenic non-human mammal described in [5], wherein the pathologic condition of human rheumatoid arthritis is a pathologic condition showing further one or more of the following (8) to (10):
(8) Angiitis is observed;
(9) Interstitial pneumonia, pleuritis, and the like, are observed; and
(10) Anemia is observed.

[7] The transgenic non-human mammal described in any of [1] to [4], wherein the pathologic condition of human rheumatoid arthritis is a pathologic condition showing all of the following (1) to (7):
(1) Joint swelling is observed in three places or more in the whole body;
(2) Symmetry joint swelling is observed;
(3) Joint swelling lasting for a week or more is observed;
(4) Destruction, ankylosis, or deformity of bones in the extremities is observed;
(5) Infiltration of lymphoid cells is observed;
(6) Cartilage destruction and bone destruction due to formation of granulation tissue are observed; and
(7) Joint deformity progresses through early stage (stage I) and moderate stage (stage II).

[8] The transgenic non-human mammal described in any of [1] to [4], wherein the pathologic condition of human rheumatoid arthritis is a pathologic condition showing all of the following (1) to (10):
(1) Joint swelling is observed in three places or more in the whole body;
(2) Symmetry joint swelling is observed;
(3) Joint swelling lasting for a week or more is observed;
(4) Destruction, ankylosis, or deformity of bones in the extremities is observed;
(5) Infiltration of lymphoid cells is observed;
(6) Cartilage destruction and bone destruction due to formation of granulation tissue are observed;
(7) Joint deformity progresses through early stage (stage I) and moderate stage (stage II);
(8) Angiitis is observed;
(9) Interstitial pneumonia, pleuritis, and the like, are observed; and
(10) Anemia is observed.

[9] The transgenic non-human mammal described in any [1] to [8], wherein species (genera) of the transgenic non-human mammal is any one selected from the group consisting of mouse, rat, guinea pig, hamster, rabbit, dog, cat, sheep, pig, cow, and horse.

[10] The transgenic non-human mammal described in any of [1] to [8], wherein species (genera) of the transgenic non-human mammal is a mouse.

[11] A method of producing a transgenic non-human mammal, the method including a step of:
introducing a foreign DNA into a cell in an early stage, the foreign DNA having a DNA which is selected from the group consisting of an MHC class II transactivator gene, an active region of the MHC class II transactivator gene, and a mutant of the MHC class II transactivator gene (having a master switch function for controlling an expression of the MHC class II genes) and which is located under the control of a type II collagen promoter.

[12] The method of producing a transgenic non-human mammal described in [11], wherein the foreign DNA includes a type II collagen enhancer.

[13] An expression vector including:
a type II collagen promoter;
a DNA sequence located downstream from the type II collagen promoter and selected from the group consisting of a MHC class II transactivator gene, an active region of the MHC class II transactivator gene, and a mutant of the MHC class II transactivator gene (having a master switch function for controlling an expression of the MHC class II genes); and
a type II collagen enhancer.

[14] A screening method of a drug for human rheumatoid arthritis, the method including the following steps (a) to (c):
(a) inducing pathologic conditions of human rheumatoid arthritis in the transgenic non-human mammal described in any of claims 1 to 10;
(b) administering a test substance to the transgenic non-human mammal; and
(c) examining whether symptoms characteristic of human rheumatoid arthritis is relieved.

[15] The screening method described in [14], wherein the step (c) determines whether one or more of the symptoms selected from the following (1) to (10) is relieved:
(1) Joint swelling is observed in three places or more in the whole body;
(2) Symmetry joint swelling is observed;
(3) Joint swelling lasting for a week or more is observed;
(4) Destruction, ankylosis, or deformity of bones in the extremities is observed;
(5) Infiltration of lymphoid cells is observed;
(6) Cartilage destruction and bone destruction due to formation of granulation tissue are observed;
(7) Joint deformity progresses through early stage (stage I) and moderate stage (stage II);
(8) Angiitis is observed;
(9) Interstitial pneumonia, pleuritis, and the like, are observed; and
(10) Anemia is observed.

[16] A screening method of a drug for human rheumatoid arthritis, the method including the following steps (A) to (C):
(A) preparing a test group and a control group, the test group including one individual or more of the transgenic non-human mammal described in any of claims 1 to 10 in which a pathologic condition of human rheumatoid arthritis is induced;
(B) administering a test substance to each individual of the test group; and
(C) comparing the degree of symptoms characteristic of human rheumatoid arthritis between the test group and the control group.

[17] The screening method described in [16], wherein the step (C) compares one or more of the symptoms selected form the following (1) to (10) between the test group and the control group:
(1) Joint swelling is observed in three places or more in the whole body;
(2) Symmetry joint swelling is observed;
(3) Joint swelling lasting for a week or more is observed;
(4) Destruction, ankylosis, or deformity of bones in the extremities is observed;

(5) Infiltration of lymphoid cells is observed;
(6) Cartilage destruction and bone destruction due to formation of granulation tissue are observed;
(7) Joint deformity progresses through early stage (stage I) and moderate stage (stage II);
(8) Angiitis is observed;
(9) Interstitial pneumonia, pleuritis, and the like, are observed; and
(10) Anemia is observed.

BRIEF DESCRIPTION OF THE DRAWINGS

FIG. 3 shows calculation criteria of clinical score.

BEST MODE FOR CARRYING OUT THE INVENTION

Figure 1:
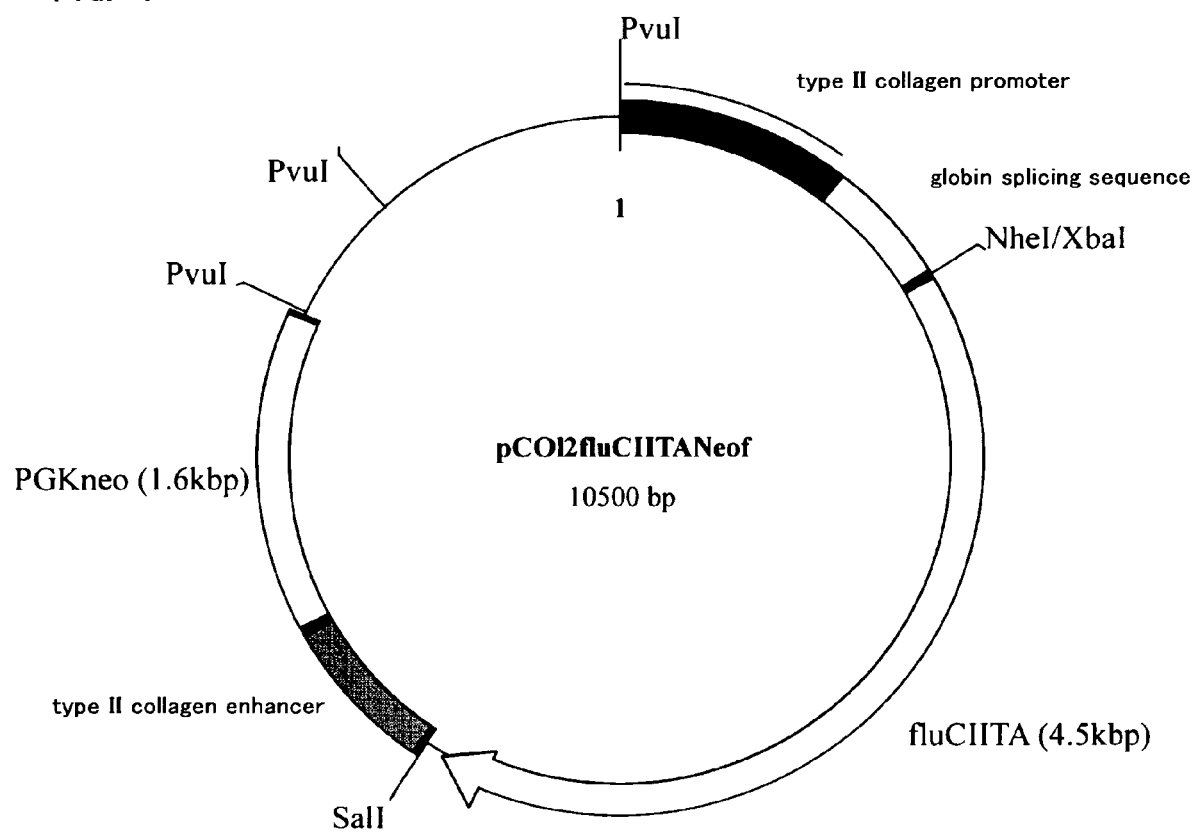
FIG. 1 shows an example of a transgene (vector pCol2fluCIITANeof in which a CIITA gene is located under the control of a type II collagen promoter) that can be used for producing a transgenic mouse of the present invention. 1) Human globin splicing sequence is located downstream from a rat type II collagen promoter site (about 1 kbp). 2) Immediately downstream from this sequence, human CIITA cDNA (fluCIITA) including a human CIITA poly A site is inserted, and following this, a rat type II collagen enhancer is located. 3) Further downstream from this, a cassette including a mammal cell non-resistant drug marker Neo gene and poly A signal is located immediately downstream from a PGK promoter. 4) A backbone vector is pBR322 having a drug (e.g. ampicillin)-resistant gene.

A first aspect of the present invention relates to a transgenic non-human mammal into which a predetermined foreign DNA is incorporated (hereinafter, transgenic non-human mammal will be also referred to as "TG animal").

The "transgenic non-human mammal (TG animal)" indicates a non-human mammal in which a foreign DNA is incorporated at the early stage of development, so that all cells constituting the mammal come to have the foreign DNA, or offspring of the mammal (offspring holding the foreign gene). The species (genera) of the mammal herein is not particularly limited and includes a mouse, rat, guinea pig, hamster, rabbit, dog, cat, sheep, pig, cow, horse, and the like. Preferable species (genera) is a rodent, for example, a mouse (for example, H-$2^q$ mouse DBA/J line and B10.Q line, or H-$2^r$ mouse R10.RIII line (these mice are available from CHARLES RIVER LABORATORIES JAPAN INC.)) and a rat (for example, Lewis ($Rt^w$), WFC ($Rt^e$), DA ($Rt^a$) rats (these rats are available from CHARLES RIVER LABORATORIES JAPAN INC.)), and the like. The most preferable species is a mouse.

The foreign DNA of the present invention includes a class II transactivator gene (hereinafter, also referred to as "CIITA gene") as a gene (transgene) used to be expressed in a TG animal. The CIITA gene is known to function as a master switch for controlling the expression of a MHC class II gene group (Steimle V., Often L. A., Zufferey M., and Mach B. 1993. Complementation Cloning of an MHC class II transactivator mutated in hereditary MHC class II deficiency. *Cell*. 75:135.). The CITTA genes of human, mouse, rat, etc. can be used. Note here that the sequence of human CIITA gene (Genbank Accession No. (hereinafter, referred to as "AN"): X74301) is set forth in SEQ ID No. 1. Similarly, the sequence of the mouse CIITA gene (AN: NM_007575) is set forth in SEQ ID No. 2. Instead of the CIITA gene, a mutant thereof may be used. The "mutant" herein is a gene having the identical or homologous sequence to a part of the sequence of the CIITA gene but having difference between the sequences when both entire sequences are compared with each other. An example of the mutant of the CIITA gene may include a DNA sequence including substitution, deletion, insertion and/or addition of one or a plurality of nucleotide bases based on the DNA sequence of the CIITA gene. Specific examples of the mutant of the CIITA gene may include a DNA sequence encoding an activation domain of an MHC class II activator factor, and a DNA sequence corresponding to a specific mRNA generated by selective splicing when an MHC class II transactivator gene is expressed. Any mutants can be used as long as they have a function specific to the CIITA gene, that is, a function as a master switch for controlling the expression of the CIITA gene group. Note here that the mutant may be naturally existing one or one artificially constructed by genetic engineering technique.

The number of copies of the transgene is not particularly limited, but it is, for example, 1 to 100. Furthermore, the TG animal of the present invention may be homozygote or heterozygote with respect to transgene.

The foreign DNA of the TG animal of the present invention includes a type II collagen promoter in addition to the CIITA gene. The origin (species) of the type II collagen promoter is not particularly limited and type II collagen promoter of a mouse or rat, a human type II collagen promoter, or the like, can be used. Note here that a sequence of human type II collagen promoter (see Nunez A. M., Kohno K., Martin G. R. and Yamada Y. 1986. Promoter region of the human pro-a1 (II)-collagen gene. *Gene,* 44:11.) is set forth in SEQ ID No. 3. Similarly, a sequence of a rat type II collagen promoter (see: Kohno K., Sullivant M., and Yamada Y. 1985. Structure of the promoter of the rat type II procollagen gene. *JBC,* 260:4441.) is set forth in SEQ ID No. 4. As the type II collagen promoter of the present invention, needless to say, the full length of those well-known sequences may be used. Furthermore, as long as the promoter activity is exhibited, only a partial region may be used. Furthermore, these well-known type II collagen promoters, which have been subjected to partial modification, can be used as a promoter in the foreign DNA as long as the promoter activity is not significantly deteriorated. Herein, "partial modification" denotes substitution, deletion, insertion and/or addition of one or a plurality of nucleotide bases (preferably one, one or two, one to three, one to four, one to five, one to six, one to seven, one to eight, or one to nine). Such a modification may be carried out in a plurality of places.

In the foreign DNA, the CIITA gene or the mutant thereof (hereinafter, referred to as "CIITA gene and the like") is located under the control of the type II collagen promoter. The term "located under the control of . . . " indicates that the CIITA gene is coupled to the type II collagen promoter directly or via another sequence so that the type II collagen promoter works so as to enable the transcription of the CIITA gene and the like. The CIITA gene and the like is usually located downstream from the type II collagen promoter and in the vicinity thereof.

It is preferable that the foreign DNA includes an enhancer for activating the transcription of the CIITA gene and the like. The "enhancer" indicates a sequence for enhancing the transcription activity by directly or indirectly acting on the promoter. In general, the enhancer acts on the promoter from a distant place. The position of the enhancer in the foreign DNA may be the upstream side or downstream side of the promoter. The enhancer is not particularly limited as long as it can enhance the transcription activity by acting on the type II collagen promoter used for the foreign DNA. For example, a type II collagen enhancer of human, mouse, rat, and the like, can be used. It is preferable that the origin of the type II collagen promoter is the same as that of the enhancer (for example, when a promoter derived from human is used, an enhancer derived from human is used), though the origin of the type II collagen promoter is not necessarily the same as that of the enhancer. By employing such a combination of the promoter and enhancer, high activity of the transcription can be obtained. Furthermore, this can be used for different kinds of animals. An example of the enhancer, the sequence of a rat type II collagen enhancer (AN: L48618) is set forth in SEQ ID No. 5. As the type II collagen enhancer of the present invention, needless to say, the full length of the well-known sequence may be used. As long as the transcription activator effect is obtained, only a partial region may be used. Furthermore, these well-known type II collagen enhancers, which have been subjected to partial modification, can be used as an enhancer in the foreign DNA as long as the transcription activation effect is not significantly deteriorated. Herein, "partial modification" denotes substitution, deletion, insertion and/or addition of one or a plurality of nucleotide bases (preferably one, one or two, one to three, one to four, one to five, one to six, one to seven, one to eight, or one to nine). Such a modification may be carried out in a plurality of places.

As one of the features of the TG animal of the present invention, pathologic conditions of human rheumatoid arthritis are represented when a type II collagen is administered. In other words, in the TG animal of the present invention, as a result of the administration of the type II collagen, pathologic conditions of human rheumatoid arthritis are induced. For example, a type II collagen derived from human, bird, cow, pig, rat, deer, chicken, mouse, or the like, can be used. The type II collagen may be derived from the same species of an animal to be administered or the species from different animals. Also besides the type II collagen, any agents capable of being used for inducing the pathologic conditions of human rheumatoid arthritis may be used. A method of administering the type II collagen (or other antigens similarly inducing the pathologic conditions of human rheumatoid arthritis) can include subcutaneous, intravenous, intraarterial, intramuscular, intraperitoneal injections, and the like. Typically, the pathologic conditions of human rheumatoid arthritis can be induced by administering the type II collagen or the like twice or more at time interval. However, as long as sufficient induction effect can be exhibited, the type II collagen or the like may be administered only once. The dose amount of the type II collagen or the like is set so that it is a sufficient amount to induce the pathologic conditions of human rheumatoid arthritis. Specifically, for example, when the TG animal is a mouse and the type II collagen is administered, the dose amount for each administration is set to be 0.001 mg to 0.05 mg, and preferably, 0.01 mg to 0.05 mg. In an $H-2^q$ haplotype mouse that has been conventionally used as a model animal of human rheumatoid arthritis, such a small dose amount of the type II collagen cannot induce the pathologic conditions of human rheumatoid arthritis satisfactorily. In other words, the TG animal of the present invention has higher sensitivity showing the pathologic conditions of human rheumatoid arthritis than the $H-2^q$ haplotype mouse that has been conventionally used as a model animal of human rheumatoid arthritis.

It is preferable that each administration is carried out in a plurality of sites of the whole body for the purpose of inducing a good immunization reaction.

Human rheumatoid arthritis is characterized by chronic, lingering and progressive symptoms. In a model mouse (collagen-induced arthritis: CIA) showing the symptoms of human rheumatoid arthritis, which has been developed to date, arthritis progresses rapidly by administration of type II collagen. In such a model mouse, it has been difficult to observe the chronic, lingering and progressive symptoms occurring in human rheumatoid arthritis. On the contrary, in the TG animal of the present invention, the symptoms of human rheumatoid arthritis progress gradually over the long time. Human rheumatoid arthritis progresses from stage I (early), stage II (moderate), stage III (advance) to stage IV (terminal). The TG animal of the present invention presents the change of symptoms similar to those of human rheumatoid arthritis. In particular, the conditions at stages I and II can be observed.

Herein, specific symptoms and findings that characterize "pathologic conditions of human rheumatoid arthritis" are listed below.

(1) Joint swelling is observed in three places or more in the whole body.

(2) Symmetry joint swelling is observed.

(3) Joint swelling lasting for a week or more is observed.

(4) Destruction, ankylosis, or deformity of bones in the extremities is observed.

(5) Infiltration of lymphoid cells is observed.

(6) Cartilage destruction and bone destruction due to formation of granulation tissue are observed.

(7) Joint deformity progresses through early stage (stage I) and moderate stage (stage II).

The more the characteristics mentioned in (1) to (7) are included, the better the pathologic conditions of human rheumatoid arthritis are represented. Therefore, it is preferable that the TG animal of the present invention has two or more of characteristics (1) to (7) (for example, the above-mentioned characteristics (1) and (2), (1) to (3), (1) to (4), (1) to (5), (4) and (5), and (4) to (6)). Most preferably, the TG animal of the present invention has all of the above-mentioned characteristics (1) to (7).

Note here that the characteristics (1) to (3) can be confirmed by the evaluation of the appearance (redness and swelling in the joints of the extremities, etc.) and the analysis using infrared thermography, histological evaluation at autopsy, and the like (as to (3), the change over time is examined). The characteristic (4) can be confirmed by the evaluation of the appearance, evaluations by X-ray imaging and by magnetic resonance imaging, histological evaluation at autopsy, and the like. The characteristics (5) to (7) can be confirmed by evaluations over time by X-ray imaging and by magnetic resonance imaging, histological evaluation at autopsy, and the like.

In general, the following complications are associated with human rheumatoid arthritis. Therefore, accompanying of such complications is an index that pathologic conditions of human rheumatoid arthritis are represented. That is to say, when the following complications are observed, a TG animal represents human rheumatoid arthritis better.

(8) Angiitis is observed.

(9) Interstitial pneumonia, pleuritis, and the like, are observed.

(10) Anemia and the like is observed.

The higher the number of complications observed becomes, the better the pathologic conditions of human rheumatoid arthritis are represented. Therefore, it is preferable that the TG animal of the present invention has two or more characteristics selected from the characteristics (8) to (10) (for example, the above-mentioned characteristics (8) and (9), (9) and (10), and (8) and (10)). Most preferably, the TG animal of the present invention has all of the above-mentioned complications (8) to (10).

Note here that the characteristics (8) and (9) can be confirmed by the measurement of blood inflammation marker, and histological evaluation, and the like. The characteristics (10) can be confirmed by hematocrit value, mean blood count, and the like, measured by blood cell count.

The method of creating a TG animal of the present invention includes a microinjection method of directly injecting DNA into the pronucleus of a fertilized egg, a method using a retrovirus vector, a method using ES cells, and the like. Hereinafter, the microinjection method using a mouse is described as a specific example of the method of creating the TG animal of the present invention.

In the microinjection method, firstly, a fertilized egg is taken from the oviduct of a female mouse that has been confirmed to have the mating, and the fertilized egg is cultivated, followed by injecting a subject DNA construct (foreign DNA) into the pronucleus. The form of the DNA construct is not particularly limited and is preferably linear or circular form from the viewpoint of the incorporation efficiency. It is particularly preferable to use a DNA construct that has been prepared in linear form. A DNA construct is prepared so that a gene to be introduced is incorporated into chromosome efficiently and the excellent expression is obtained. The DNA construct includes the above-mentioned CIITA gene and the like and type II collagen promoter (if necessary, the DNA construct includes appropriate enhancer sequence, selected marker, replication origin, terminator sequence, and the like).

The fertilized egg to which injection has been completed is transplanted to the oviduct of a pseudopregnant mouse. By breeding the mouse having undergone transplantation, a child mouse (F0) is obtained. In order to confirm that transgene is appropriately incorporated into the chromosome of the child mouse, DNA is extracted from, for example, a tail of the child mouse and it is subjected to Southern hybridization analysis, slot blot (dot blot) analysis, PCR analysis, and the like.

Next, the identified transgenic individual is subjected to mating with another mouse. The "another mouse" herein can include a $H-2^q$ or $H-2^r$ haplotype mouse, a MRL-1 or a substrain of a MRL-1pr$^+$ mouse, a NZB/KN mouse, a SKG mouse, a NOD mouse, a scid/scid mouse, a RAG2-deficient mouse, or a Lewis rat, or the like (these mice are available from, for example, CHARLES RIVER LABORATORIES JAPAN INC.). Alternatively, other transgenic individuals obtained as a result of the above-mentioned operation can be used. Among them, it is preferable to use an $H-2^q$ haplotype mouse. The $H-2^q$ haplotype mouse shows symptoms of human rheumatoid arthritis with high frequency in response to the type II collagen while no difference is observed between male animal and female animal. Therefore, use of this can provide a TG mouse that represents pathologic conditions of human rheumatoid arthritis well. Note here that the $H-2^q$ haplotype mouse does not show the symptoms of human rheumatoid arthritis under normal breeding conditions. Furthermore, the $H-2^q$ haplotype mouse does not show the symptoms of human rheumatoid arthritis unless the induction is carried out after this transgene is incorporated.

As mentioned above, the TG animal of the present invention presents pathologic conditions of human rheumatoid arthritis. Therefore, the TG animal of the present invention is an effective means (model animal) for studying human rheumatoid arthritis. In particular, use of the TG animal of the present invention enables search for drugs for human rheumatoid arthritis and studying of the effects of the drugs. Consequently, a treatment method for human rheumatoid arthritis can be established. Thus, as a second aspect, the present invention relates to a screening method of drugs for human rheumatoid arthritis using the above-mentioned TG animal.

The screening method of the present invention includes a step (step a) of inducing pathologic conditions of human rheumatoid arthritis in the above-mentioned TG animal of the present invention; a step (step b) of administering a test substance to the TG animal; and a step (step c) of examining whether or not the symptoms characteristic of human rheumatoid arthritis is improved in the TG animal.

Note here that in this specification, "drug for human rheumatoid arthritis" includes not only a drug used for improving the symptoms of a patient with human rheumatoid arthritis (including prevention of the development of a certain symptom) but also a drug used for the purpose of preventing the development of human rheumatoid arthritis by administering it to a patient who may develop human rheumatoid arthritis. Furthermore, the tern is also intended to include a drug for preventing the complications caused by human rheumatoid arthritis or for improving the symptoms of complications. Thus, drugs obtained by using the screening method of the present invention can be also used for the purpose of prevention or treatment of complications of human rheumatoid arthritis.

In the step a, typically, by the administration of type II collagen, pathologic conditions of human rheumatoid arthritis are induced. However, any antigens other than the type II collagen, which can act on directly or indirectly the CIITA introduced into the TG animal of the present invention so as to activate thereof, or any antigens capable of being bonded to histocompatibility complex ectopicly produced and induced by CIITA in the cartilage cells can be used for inducing pathologic conditions of human rheumatoid arthritis. That is to say, any antigen that is to be a cause in human rheumatoid arthritis or substances (inducers) capable of inducing the antigen substance can be used as an inducer. Specific examples of the inducer can include proteoglycan, pristane (2,6,10,4-tetramethylpentodecan), cationic antigen, sonicated Staphylococcal cell wall, lipopolysaccharide, in addition to antigen such as type II collagen. The administration form (administration method, dosage, and the like) of type II collagen, and the like, is a form that is capable of inducing the pathologic conditions of human rheumatoid arthritis in the TG animal and does not affect the subsequent operations. An example of the administraion methods can include subcutaneous, intravenous, intraarterial, intramuscular, or intraperitoneal injections. For example, when the TG animal is a mouse and the type II collagen is administered, the dosage for each administration is set to be 0.001 mg to 0.05 mg, and preferably, 0.01 mg to 0.05 mg. When the dosage is too small, a sufficient inducing effect cannot be obtained. On the contrary, when the dosage is too large, it is not preferable because immunization stimulation more than necessary is applied. In order to induce the pathologic conditions of human rheumatoid arthritis reliably, it is preferable that type II collagen is administered twice or more.

The type II collagen derived from, for example, human, bird, cow, pig, rat, or mouse can be used. Type II collagens derived from various kinds of species are commercially available and in the present invention, such commercially available type II collagens can be used preferably. Needless to say, according to the conventional method, type II collagen prepared by a biochemical technique, a genetic engineering technique, and the like, may be used.

Hereinafter, a specific example of the method of inducing pathologic conditions of human rheumatoid arthritis by the administration of type II collagen is shown (an example of a case in which the TG animal is a mouse). Firstly, as a primary immunization, 0.01 mg of type II collagen (for example, a mixture obtained by dissolving type II collagen with high purity (for example, purity: 99%), which has been extracted and purified from cow articular cartilage in the usual manner, into 0.01M acetic acid, and mixing this solution with an equal amount of complete adjuvant) is administered to a several places of a TG mouse by subcutaneous injection. After the TG mouse is bred for three weeks, 0.01 mg of type II collagen (which has been prepared by the same method as in the primary immunization except that incomplete adjuvant has been used) is administered to a several places of the TG noise by subcutaneous injection again as a secondary immunization. After the secondary immunization, the TG mouse is examined for redness, swelling, and the like, by monitoring the joints of the extremities. Thus, it is confirmed that the symptoms of human rheumatoid arthritis are induced. If necessary, the presence of the complications is examined at autopsy.

An example of the method of administering a test substance in the step b can include oral administration, intravenous, intraarterial, subcutaneous, intramuscular, intraperitoneal injection, or the like.

As the test substance, organic compounds having various molecular sizes (nucleic acid, peptide, protein, lipid (simple lipid, complex lipid (phosphoglyceride, sphingolipid, glycosylated glyceride, cerebroside, and the like), prostaglandin, isoprenoid, terpene, steroid, and the like)), or an inorganic compound can be used. The test substance may be naturally occurring or may be synthesized. In the latter case, for example, an efficient screening system can be constructed by using, for example, a combinatorial synthesizing method. Note here that a cell extract, culture supernatant, and the like, may be used as the test substance.

The symptoms characteristic of human rheumatoid arthritis in the step c includes, for example, the following (1) to (7) as mentioned above: (1) Joint swelling is observed in three places or more in the whole body; (2) Symmetry joint swelling is observed; (3) Joint swelling lasting for a week or more is observed; (4) Destruction, ankylosis, or deformity of bones in the extremities is observed; (5) Infiltration of lymphoid cells is observed; (6) Cartilage destruction and bone destruction due to formation of granulation tissue are observed; and (7) Joint deformity progresses through early stage (stage I) and moderate stage (stage II). Typically, in the step c, at least one of the above-mentioned symptoms (1) to (7) is examined for the change (whether the symptoms are improved or not).

In addition to these symptoms or instead of these symptoms, the complications of human rheumatoid arthritis (for example, as mentioned above, (8) Angiitis is observed; (9) Interstitial pneumonia, pleuritis, and the like, are observed; and (10) Anemia and the like is observed) may be examined. When a plurality of symptoms are examined, the symptoms are arbitrarily combined. For example, the combination of (1) and (2), the combination of (1) to (3), the combination of (1) to (4), the combination of (1) to (5), the combination of (1) to (6), the combination of (1) to (7), the combination of (2) to (4), the combination of (3) to (6), the combination of (7) and (8), and the combination of (7) to (9), and the like, may be employed. In general, it is thought that as the number of symptoms to be improved is increased, the efficacy of the test substance is increased. Therefore, it is preferable that more symptoms are examined in the step c. However, when not less than predetermined correlation between two symptoms is observed, only one of the two symptoms may be examined.

In the step c, when the symptoms to be tested are improved, it is determined that the test substance has a treatment effect (including prevention effect) to human rheumatoid arthritis (or the complications thereof) and is a potential drug candidate. Furthermore, the effect of the test substance can be determined by using the delay of progress in specific symptoms as an index. That is to say, in the step c. when the progress of the symptoms to be tested is delayed, it may be determined that the test substance is a potential candidate of the treatment drug for human rheumatoid arthritis. In the case of using the delay of progress in the certain symptoms as an index, by previously measuring the transition of the progress (criteria) of the symptoms when the test substance is not administered, the effect of the test substance may be determined based on the criteria.

Preferably, a group (test group) including TG animals in which pathologic conditions of human rheumatoid arthritis are induced and to which a test substance is administered and a group (control group) including the above-mentioned TG animals and to which a test substance is not administered are prepared. After a test substance is administered to the test group, the degree of symptoms characteristic of human rheumatoid arthritis is compared between the test group and the control group. As a result of the comparison, for example, when it is confirmed that the symptoms to be tested are improved or that the progress of the symptoms is delayed in the test group rather than the control group, it can be determined that the test substance is a potential candidate for drugs for human rheumatoid arthritis. In this way, by comparing the group (test group) to which the test substance is administered and the group (test group) to which the test substance is not administered, the efficacy of the test substance can be determined easily and with high reliability. Note here that firstly, a plurality of TG animals prepared may be divided into a test group and a control group, and then type II collagen or the like may be administered to each group so as to induce the pathologic conditions of human rheumatoid arthritis. Alternatively, the type II collagen or the like may be administered to the plurality of TG animals prepared so as to induce the pathologic conditions of human rheumatoid arthritis, and then the TG animals may be divided into the test group and the control group.

The numbers of individuals included in the test group and the control group are not particularly limited. In general, as the number of individuals is increased, highly reliable results can be obtained. However, handling a large number of individuals at the same time involves the difficulty in securing and operating (including breeding) the animals. Therefore, it is preferable that the number of animals included in each group is 1 to 50, preferably 2 to 30 and further preferably 5 to 20.

When the compound selected by the screening method of the present invention has a sufficient effect to human rheumatoid arthritis (or the complications thereof), the compound can be used as the active agent of the drug as it is. On the other hand, when the compound does not have a sufficient effect, the compound, which has undergone modification such as chemical modification to enhance the drug efficacy, can be used as an active agent of drugs for human rheumatoid arthritis. Needless to say, even when the compound has a sufficient drug efficacy, the compound may undergo Such a modification for further enhancing the drug efficacy.

Unless otherwise specified, the genetic engineering operation of this specification may be carried out with reference to, for example, Molecular Cloning (Third Edition, Cold Spring Harbor Laboratory Press, New York) or Current protocols in molecular biology (edited by Frederick M. Ausubel et al., 1987).

EXAMPLE 1

Creation of Transgenic Mouse into which MHC Class II Transactivator Gene (CIITA Gene) is Introduced As mentioned below, a transgenic mouse into which a CIITA gene was introduced was created according to Manipulating the mouse embryo, a laboratory manual, second edition, Brigid Hogan et al., Cold Spring Harbor Laboratory Press.

1. Preparation of Vector for Introducing Gene (Foreign DNA)

Vector pCol2fluCIITANeof (see FIG. 1), in which an MHC class II transactivator gene (CIITA gene) was located under the control of a type II collagen promoter, was constructed by the following procedures. This vector has the following characteristics: 1) A human globin splicing sequence is located downstream from about 1 kbp rat type II collagen promoter region. 2) Immediately downstream from this, human CIITA cDNA including a human CIITA poly A site is inserted. Following to this, a rat type II collagen enhancer is located. 3) Further downstream from this, a cassette is located immediately downstream from a PGK promoter. In the cassette, a drug marker Neo gene being non-resistant to mammal cells and a poly A signal are located. 4) As a backbone vector, DNA for recombination used for a usual cloning using Escherichia coil can be used. For this vector, pBR322 having a drug (e.g. ampicillin)-resistant gene was used. 5) A Pvul restriction enzyme site is included so that a vector portion of the backbone derived from Escherichia coil can be excluded in advance.

Finally, the vector constructed by the above-mentioned procedures was treated with a Pvul restriction enzyme so as to exclude the backbone vector region derived from *Escherichia coli* and to become linear. The linear DNA was purified by using beads and the like exhibiting a DNA binding property, so that a transgene for injection was obtained. It is confirmed that when the obtained transgene is introduced into MG615 cell that is a mouse cartilage cultivation cell line, MHC class II protein is expressed on the surface of the cell. DNA is stored in a state in which it is adjusted to 30 to 100 µg/ml with 10 mM Tris/0.2 mM EDTA buffer.

2. Introduction of Foreign DNA 2-1. Preparation of Mouse

As a mouse line used for preparing a chimeric mouse, F1 generation obtained by crossing SDB/DBA was employed. A fertilized egg was prepared according to a conventional method and used for injection.

2-2. Preparation of Fertilized Egg

HCG is injected according to a conventional method and a fertilized egg is obtained from the ovary of couplated female mouse. After the pronuclei and granule in the fertilized egg are confirmed, the fertilized egg is used for microinjection.

2-3. Microinjection into Fertilized Egg Pronucleus

Two hundreds fertilized eggs for each microinjection are used. DNA is injected by using a micromanipulator. As DNA to be injected, DNA which has been finally adjusted to 3 µg/ml and then filtrated through a 0.22 µm filter, is used.

2-4. Transplantation in the Oviduct

A pseudo-pregnant mouse, which is used as a foster mother, is prepared. An embryo into which DNA has been injected is directly transplanted into the oviduct of foster mother. Alternatively, the embryo is cultured for one day to ensure the embryo division, and thereafter the embryo was transplanted. Twenty-five to thirty-five embryos are transplanted in one animal.

3. Identification of Transgenic Mouse

The obtained transgenic mouse was identified by Southern blotting. After weaning, DNA was extracted from the mouse tail and analyzed. As a probe used for Southern blotting, a coding region at C terminal of CIITA (positions 2978 to 3329 of human CIITA DNA sequence (SEQ ID No. 1)) was used. Mice in which about 10 copies of the gene have been incorporated were used for back-crossing with DBA mouse. The gene introduced into the mouse was identified by Southern blotting and a PCR method.

4. Mating

The obtained transgenic mouse was allowed to back-cross with a DBA mouse. The backcross was repeated seven generations or more so as to have 99% or more of the genetic background of DBA. Thereby, the line was purified to be a genetic background. Consequently, the resultant transgenic mouse (a CIITA transgenic mouse) was used for the following experiment.

EXAMPLE 2

Induction Test of Rheumatoid Arthritis using Transgenic Mouse (1) Immunization Induction The CIITA transgenic mouse produced in Example 1 was immunized according to the following procedures. Note here that mice being litters but having no transgene and mice having a DRB/1j background were used as a wild type control 6-8 weeks old).

Firstly, as a primary immunization, 0.01 mg of type II collagen was administered to several sites by subcutaneous injection Note here that type II collagen (purity: 99%, produced by Collagen Gijutu Kensyu Kai) purified from cow articular cartilage, which was dissolved in 0.01M acetic acid and mixed with an equal amount of complete adjuvant (DIFCO), was used.

At the third week following the primary immunization, 0.01 mg of type II collagen was administered to several sites again by subcutaneous injection as a secondary immunization. For the secondary immunization, a mixture of type II collagen with incomplete adjuvant was used.

2. Confirmation of Symptoms of Rheumatoid Arthritis

Figure 2:
FIG. 2 shows results of monitoring redness, swelling, and the like, after secondary immunization is conducted on the transgenic mouse produced by a method described in Example. After secondary immunization, redness and swelling are observed over several weeks only in the transgenic mouse. Symptoms are progressive and are being deteriorated gradually. Left picture shows a CIA induced control mouse in which redness and swelling are not observed. Right picture shows a CIA induced CIITA transgenic mouse in which redness and swelling are observed.
Figure 4:
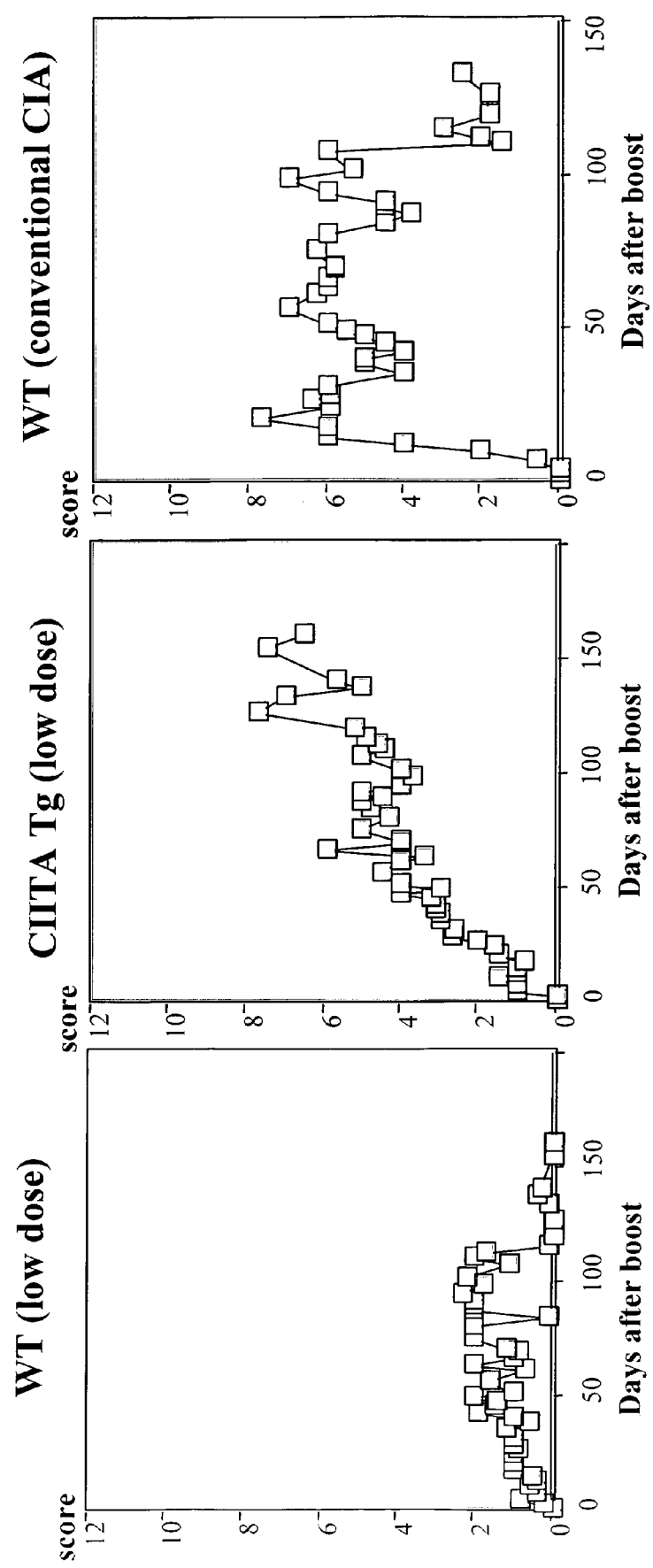
FIG. 4 illustrates graphs showing the change overtime of clinical scores. The clinical scores are calculated based on the criteria shown in Table in FIG. 3. The onset is observed at the first week following the boost in a conventional CIA method. In comparison with this, the onset is observed later such as at the fifth to sixth week following the immunization at low concentration and boost (1/20 times as the concentration in the conventional method) using a transgenic mouse and the symptoms progress gradually. Furthermore, as to the duration time of symptoms, symptoms disappear in about 100 days in the conventional CIA method while they continue for 150 days or longer in the transgenic mouse.

After the secondary immunization, redness, swelling, and the like, in the joints of the extremities were monitored. As a result, in general CIA, in several days after the secondary immunization is carried out, strong redness and swelling are observed. While in the transgenic mouse, redness and swelling in the extremities have been observed for several weeks or more (FIG. 2). In control mice, no or few of such symptoms were observed (FIG. 2). Clinical score was calculated based on the criteria shown in FIG. 3 and the results are shown in FIG. 4.

Figure 5:
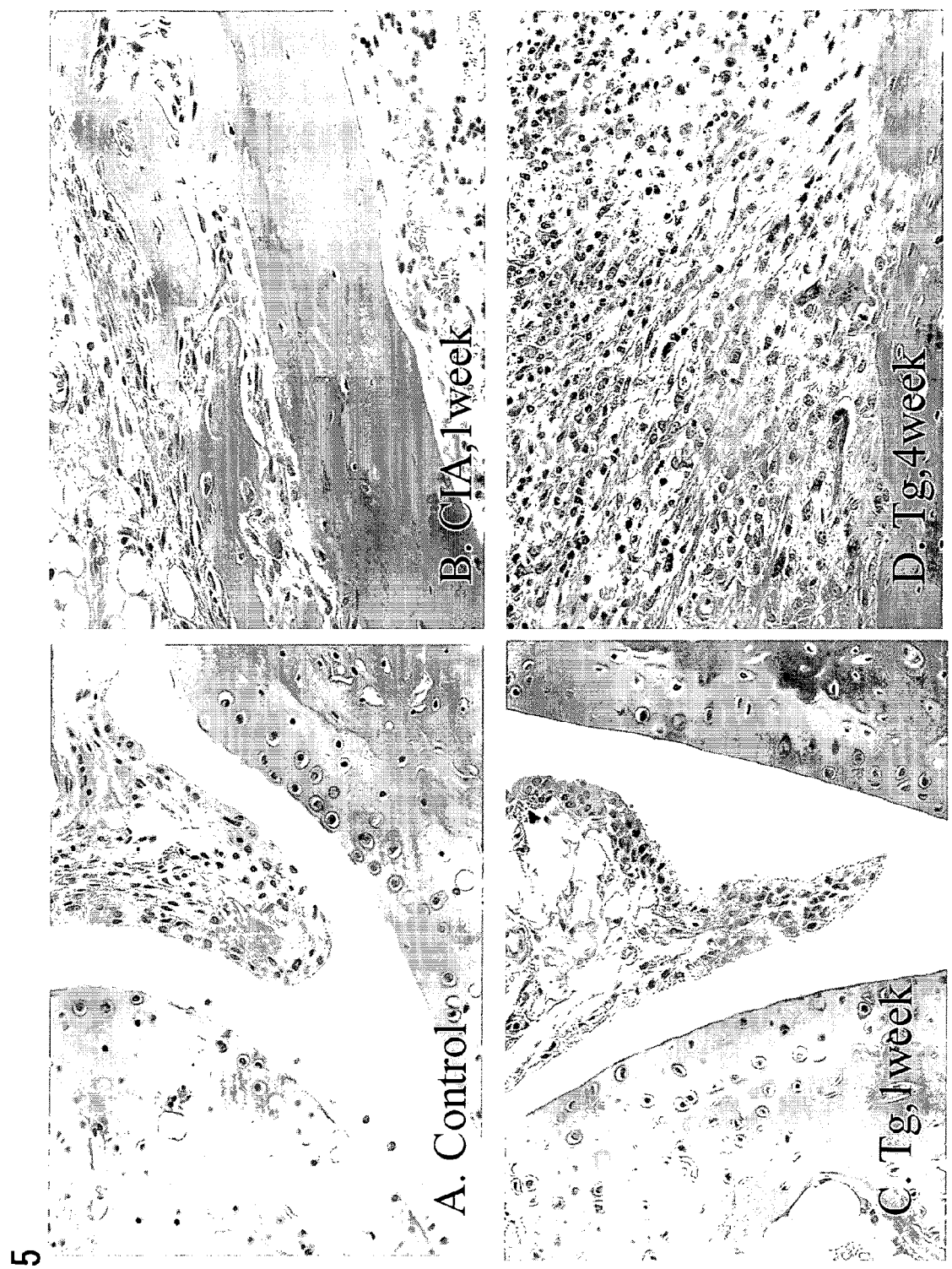
FIG. 5 shows hematoxylin- and eosin-stained images in the joint portion (secondary immunization). In a conventional CIA method, at the first week, in the joint portion, Infiltration of lymphoid cells, destruction of the cartilage and the bone tissue progress (A: control and B: CIA). On the other hand, in the transgenic mouse, destruction of the cartilage and the bone tissue, and the like, which are observed in the CIA method, are not observed at the first week (C: Tg, at the first week). Thereafter, Infiltration of lymphoid cells gradually proceeds (D: Tg, at the fourth week).
Figure 6:
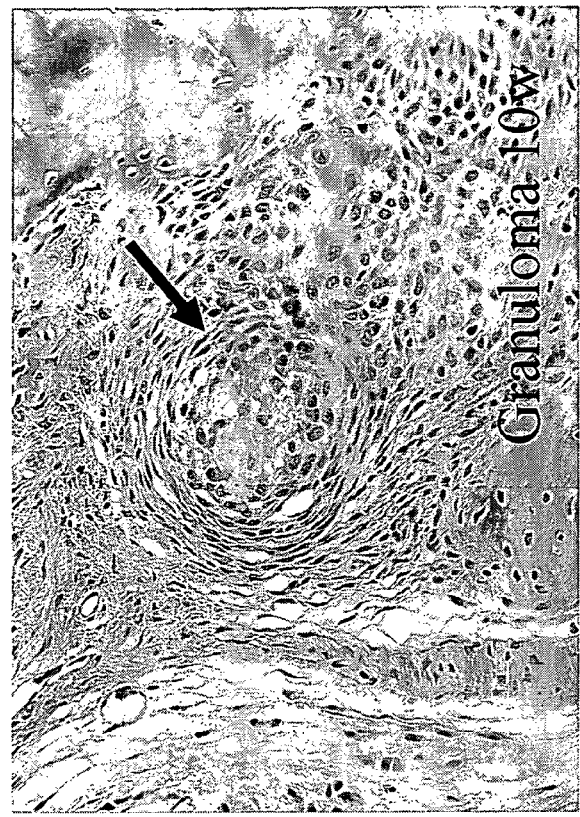
FIG. 6 shows hematoxylin- and eosin-stained images in the joint portion (at the 10th week following the secondary immunization). At this time, destruction of the cartilage and the bone tissue progress and bone deformity is observed. In addition, nodule (A) and granuloma (B) including cellular necrosis in the central portion are observed.
Figure 6:
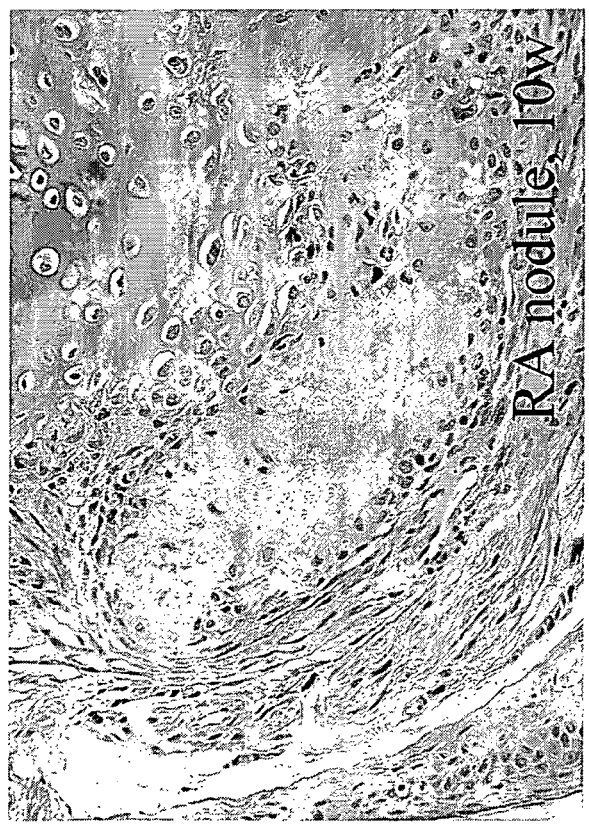

On the other hand, the monitoring by using infrared thermography and the like clearly showed that arthritis progresses in the transgenic mouse of interest. That is to say, arthritis progresses gradually over a long time. When a tissue section in the joints at this time is observed, infiltration of lymphoid cells to the peripheral portion of the joints was observed, showing the disease conditions at the early stage of human rheumatoid arthritis (FIG. 5). The monitoring is further continued. When about two months had passed, the swelling in the extremities progressed further. Although some individuals showed slight remission, basically bone destruction progresses, so that disorders such as bone deformity were observed finally (FIG. 6).

Figure 7:
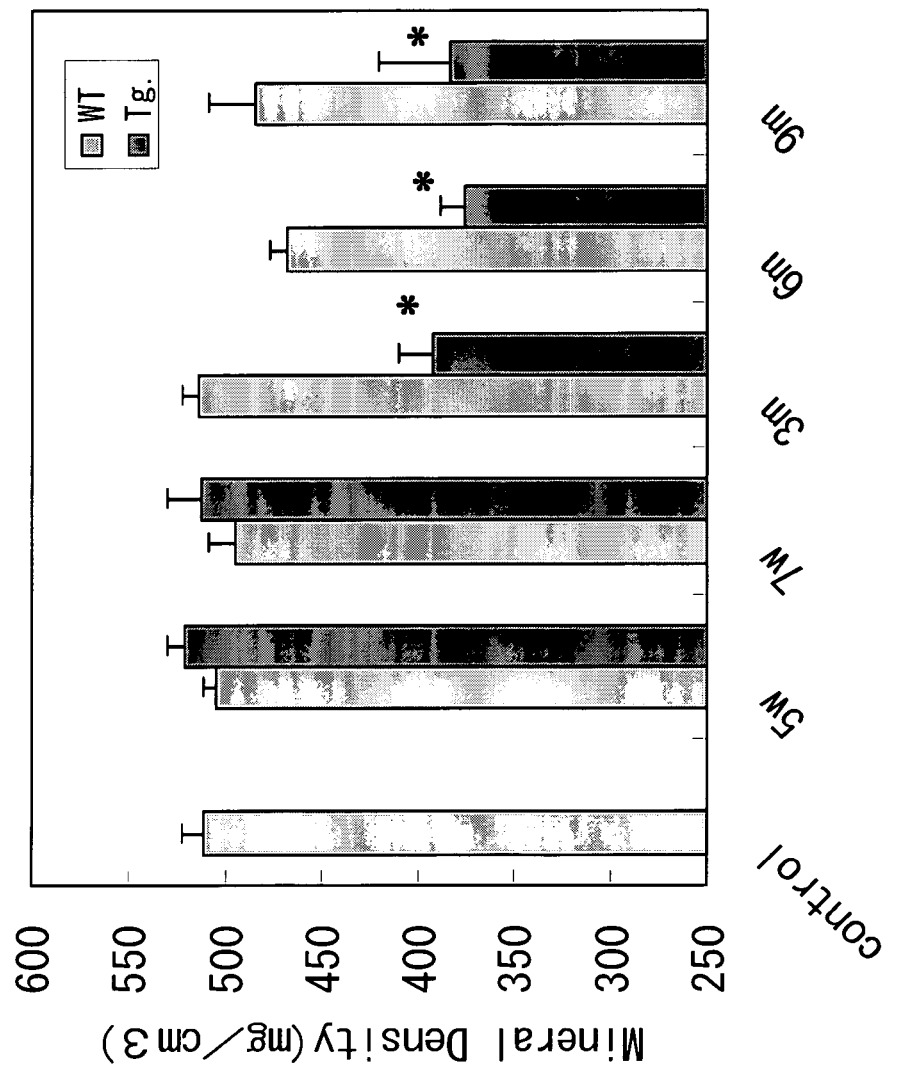
FIG. 7 is a graph showing the change over time bone mineral density measured after immunization at low concentration and boost are carried out using a transgenic mouse. In a conventional CIA method, at the fifth week, the change in the bone density is observed and no large change is shown thereafter. On the other hand, in the transgenic mouse, not only progress of inflammation but also the change in bone density gradually progresses.

Low concentration of immunization and boost were given to transgenic mice and the change over time of the bone density was measured (FIG. 7). In a conventional CIA method, at the fifth week following the immunization, the change of the bone density was observed, and large change was not shown thereafter. On the other hand, in the transgenic mouse, not only the progress of inflammation but also the change in the bone density progresses gradually.

Besides, by autopsy and blood test, entire complications are found out. For example, primary lesion of the respiratory organ, vasculitis, reduction of red blood cell count, which are caused by rheumatism, are confirmed. Furthermore, by transferring a mouse, which is usually bred and subjected to experiment in a SPF state, to a conventional breeding environment, or by inoculating a mouse with *Listeria monocytogenes* and the like under the breeding environment, it is confirmed that a secondary excessive immunization reaction and the like is induced in rheumatism conditions. In addition, an adverse effect caused by administration of the drug for rheumatism is confirmed.

INDUSTRIAL APPLICABILITY

A transgenic non-human mammal (TG animal) of the present invention represents pathologic conditions of human rheumatoid arthritis well. The TG animal of the present invention can be used as a model of human rheumatoid arthritis for the purpose of the development of drugs for human rheumatoid arthritis or elucidation of the onset mechanism of human rheumatoid arthritis. Furthermore, the TG animal of the present invention can be used for screening of drugs for complications (angiitis, articular pneumonia, and the like) caused by human rheumatoid arthritis, and for verifying the effect of the drugs. Furthermore, the TG animal of the present invention can be used as a model for developing treatment methods in the field of regeneration medicine for progressive rheumatoid arthritis.

The present invention is not limited to the description of the above embodiments and Examples of the present invention. A variety of modifications, which are within the scopes of the claims and which can be easily achieved by a person skilled in the art, are included in the present invention.

All of the articles, patents and publications cited herein are hereby incorporated by Reference.

The invention claimed is:

1. A transgenic mouse or rat whose genome comprises a foreign DNA, the foreign DNA comprising a type II collagen promoter, a MHC class II transactivator gene, and a type II collagen enhancer sequence, wherein said DNA is located under the control of said type II collagen promoter and enhancer, wherein administration of type II collagen to said transgenic mouse or rat at a dose of 0.01 mg to 0.05 mg two or more times results in presentation of pathologic conditions of human rheumatoid arthritis in said transgenic mouse or rat, wherein the pathologic conditions of human rheumatoid arthritis show the following pathologic conditions (1) to (6):

(1) Joint swelling is observed in the whole body;
(2) Joint swelling lasting for a week or more is observed;
(3) Destruction, ankylosis, or deformity of bones in the extremities is observed;
(4) Infiltration of lymphoid cells is observed;
(5) Cartilage destruction and bone destruction due to formation of granulation tissue are observed; and
(6) Joint deformity progresses through early stage (stage I) and moderate stage (stage II).

* * * * *